United States Patent
Kelleher et al.

(10) Patent No.: US 12,201,548 B2
(45) Date of Patent: Jan. 21, 2025

(54) OSTOMY BAG

(71) Applicant: OSTOFORM LIMITED, Westmeath (IE)

(72) Inventors: Kevin Kelleher, Westmeath (IE); Eoghan Spain, Westmeath (IE)

(73) Assignee: OSTOFORM LIMITED, Westmeath (IE)

( * ) Notice: Subject to any disclaimer, the term of this patent is extended or adjusted under 35 U.S.C. 154(b) by 884 days.

(21) Appl. No.: 17/058,525

(22) PCT Filed: Jun. 3, 2019

(86) PCT No.: PCT/EP2019/064296
§ 371 (c)(1),
(2) Date: Nov. 24, 2020

(87) PCT Pub. No.: WO2019/229268
PCT Pub. Date: Dec. 5, 2019

(65) Prior Publication Data
US 2021/0212856 A1    Jul. 15, 2021

(30) Foreign Application Priority Data

Jun. 1, 2018 (GB) ..................................... 1809012

(51) Int. Cl.
*A61F 5/448* (2006.01)
(52) U.S. Cl.
CPC ................................... *A61F 5/448* (2013.01)
(58) Field of Classification Search
CPC ........... A61F 5/449; A61F 5/448; A61F 5/445
See application file for complete search history.

(56) References Cited

U.S. PATENT DOCUMENTS 2,765,790 A * 10/1956 Dickson .................. A61F 5/445
604/338
4,867,749 A * 9/1989 Steer ...................... A61F 5/448
604/337

(Continued)

FOREIGN PATENT DOCUMENTS

CN         1396816 A  *  2/2003  ............. A61F 5/443
EP         0197672 A2     10/1986
(Continued)

OTHER PUBLICATIONS

International Search Report for PCT/EP2019/064296, dated Oct. 29, 2019.
Written Opinion for PCT/EP2019/064296, dated Oct. 29, 2019.

*Primary Examiner* — Rebecca E Eisenberg
*Assistant Examiner* — Matthew Wrubleski
(74) *Attorney, Agent, or Firm* — Troutman Pepper Hamilton Sanders LLP (Rochester)

(57) ABSTRACT

An ostomy bag for collecting output from a stoma comprising: a bag having at least one opening for accepting ostomy output; a spout positioned at least partially around the edge of the at least one opening; wherein the spout extends away from the at least one opening and radially outwardly from the at least one opening, into the interior of the bag. Methods of manufacturing ostomy attachments and methods of use are also provided. An attachment plate for use in an ostomy bag and an ostomy bag kit are also described. Methods of manufacturing an ostomy bag and an attachments plate, and methods od use of the same are further described.

10 Claims, 2 Drawing Sheets

(56) References Cited

U.S. PATENT DOCUMENTS 5,722,965 A * 3/1998 Kuczynski .............. A61F 5/443
                                                        604/338
2013/0053802 A1   2/2013 Maidl

FOREIGN PATENT DOCUMENTS

WO     2014063709 A1    5/2014
WO   WO-2017167582 A2 * 10/2017 ........... A61F 5/4405

* cited by examiner

OSTOMY BAG

This application is a national stage application under 35 U.S.C. § 371 of PCT Application No. PCT/EP2019/064296, filed Jun. 3, 2019, which claims the priority benefit of Great Britain Patent Application No. 1809012.6, filed Jun. 1, 2018, which are hereby incorporated by reference in their entirety.

FIELD

The invention relates to the field of ostomy bags or pouches.

BACKGROUND OF THE INVENTION

An ostomy is a surgically-created opening in the body to allow for discharge of bodily fluids, typically waste products. An ostomy is associated with a stoma, an externalising of a body cavity such as the intestine, ileum or ureter; the ostomy providing an alternative fluid outlet for that cavity via the stoma. Use of an ostomy typically follows surgery or disease that has disrupted the normal path of bodily fluids or waste through and/or from that body cavity.

The most common types of ostomy are: a colostomy, where the colon is diverted to an ostomy in the abdominal wall, typically following surgery to remove a lower part of the colon; ileostomy where a similar procedure is applied to the small intestine (the ileum); and a urostomy, where urine is drained through an ostomy where normal drainage through the bladder and ureter/urethra is not possible.

The stoma may present flush with the surface of the body at the ostomy or may protrude through the ostomy. Typically a bag or other suitable receptacle is attached to the patient's skin on an exterior face of the ostomy to collect bodily fluid as it is discharged from the stoma.

It is well documented that the bodily fluids discharged through a stoma can cause significant irritation if they come into contact with the skin surface surrounding the ostomy. It is therefore desirable to seal the connection between the ostomy and an ostomy bag that collects the waste in order to prevent the output from the stoma contacting the skin. However, the fact that each stoma is individually sized and shaped, along with the need to replace the bag and hence break the seal regularly, makes an optimum seal difficult to achieve in practice.

One known method of protecting the skin around a stoma from the stoma output is to make use of an ostomy seal. Typically formed of a biocompatible adhesive material such as hydrocolloid, an ostomy seal closely surrounds the ostomy, adhering to the skin on one side and a corresponding hydrocolloid seal around the entrance to an ostomy bag on the other.

Hydrocolloid, while providing excellent adherence and skin compatibility, is absorbent. Absorption of stomal output by the hydrocolloid seal that is in contact with the skin can lead to irritation and it is therefore desirable to minimise the contact of the hydrocolloid seal with the output from the stoma. This problem may be mitigated or eliminated by the use of a spout or other apparatus that directs the output from the stoma, typically under gravity, away from the skin into the ostomy bag.

EP0197672 describes a urostomy appliance that has a two-part form; a first part comprising a hydrocolloid adhesive pad that surrounds the stoma and a domed receptacle that is positioned over the stoma forming a seal with the hydrocolloid adhesive pad. The domed receptacle has a spout that has an entrance spaced from the skin for attachment to an ostomy bag. The spacing of the spout away from the skin does not direct the output from the stoma to the ostomy bag and allows pooling of stomal output on the hydrocolloid pad leading the instability issues and skin irritation outlined above.

WO 2017/167582 describes an ostomy attachment that addresses some of the above problems. A non-absorbent spout is attached to the hydrocolloid seal to effectively direct the output from the stoma to the ostomy bag. This helps avoid the absorbent seal material coming into contact with the ostomy output and at least reduces absorption and the skin issues deriving from this in the way described above.

The ostomy attachment of WO 2017/167582, while offering many advantages over the previously existing systems, such as EP0197672, comprises two components: an absorbent, typically hydrocolloid, seal that contacts the skin; and a non-absorbent, spout. Assembling an attachment that comprises a flexible component made of a non-absorbent materials and a seal made of absorbent material such as hydrocolloid remains a challenge because of the hydrocolloid material's propensity to lose its structural integrity as it begins to absorb effluent from a stoma. If the hydrocolloid loses its structural integrity, there may be a risk of the flexible, non-absorbent component separating from the hydrocolloid leading to output from the stoma failing to be effectively directed from the skin, leaks from the attachment, or perhaps the ostomy bag falling off.

Furthermore, prior art ostomy attachments that are currently used by patients do not comprise a spout. In these devices a seal, typically formed of hydrocolloid is applied to the skin around the stoma and then an ostomy bag is attached to this via a corresponding seal on the bag. In the device of WO 2017/167582, the spout is either provided pre-fabricated as part of the seal, in which case, the ostomy bag must be attached by the patient after negotiating the spout, or the spout must be first applied to the seal prior to attachment of the bag adding a step to the process of donning of the bag. While the majority of patients would have no difficulty in adopting the device of WO 2017/167582, it would be advantageous to offer an improved, or at least alternative solution where the spout is part of the ostomy bag, rather than the ostomy attachment such that the process of donning the bag is as similar as possible to the previous experience of the patient with prior art ostomy bags. This would have benefits in terms of simplicity, and resulting improvements in patient compliance, reducing errors in donning the ostomy bag that may otherwise lead to leaks, or the bag falling off, or waste if the incorrectly fitted bag must be discarded.

There remains a need in the art therefore for an ostomy attachment that effectively directs output from a stoma to an ostomy bag, preventing or minimising contact of the stomal output with the skin or the absorbent seal that provides a secure attachment of the ostomy bag to the skin. It is also desirable for the device to be easy for the patient to use and position.

These and other uses, features and advantages of the invention should be apparent to those skilled in the art from the teachings provided herein.

SUMMARY OF THE INVENTION

In a first aspect the invention relates to an ostomy bag for collecting output from a stoma comprising a bag having at least one opening for accepting ostomy output and a spout positioned at least partially around the edge of the at least one opening, wherein the spout extends away from the at least one opening and radially outwardly from the at least one opening into the interior of the bag.

In an embodiment, the spout extends outwardly from the interior of the bag such that an outer end of the spout rests against or near to a patient's skin when in use. In a further embodiment, the spout is configured to direct ostomy output away from a patient's skin and into the ostomy bag. In another embodiment, the spout is angled to optimise collection of ostomy output and delivery of ostomy output into an ostomy bag.

In an embodiment the spout extends a perpendicular distance from the at least one opening into the bag by between 0.5 cm and 5 cm.

In embodiments, the spout is fixedly attached to the bag. Suitably, the spout is fixedly attached to the bag via attachment to a plate positioned on an exterior of the bag. In further embodiments, the spout is fixedly attached to a plate positioned on an exterior of the bag.

In other embodiments, the bag is attached to the plate by at least one of permanent fixing and semi-permanent fixing. Suitably, permanent fixing is at least one of plastic welding, melting, screws, rivets, pins: and semi-permanent fixing is at least one of adhesive, clips, hooks, hook and loop tape, screw thread, bayonet fitting.

In embodiments, the plate is configured for attachment to a seal for fixing the ostomy bag to the patient's skin. Suitably, the plate comprises the seal. In embodiments, the plate comprises a first face and a second face and wherein the seal attaches to the first face of the plate and the bag is attached to the second face of the plate.

In embodiments, the spout comprises at least one flexible arm that extends around the at least one opening. Suitably, the spout comprises two flexible arms that extend around the at least one opening.

In embodiments, the bag has generally circular concentric markings around the at least one opening to provide the user with a guide for adjusting the size of the at least one opening. Suitably, the generally circular markings share an edge with the at least one opening adjacent with the spout.

In a second aspect the invention relates to a method for manufacturing an ostomy bag of the first aspect of the invention comprising the steps of: providing a rear impermeable layer having at least one opening; fixedly attaching a spout to a section of the edge of the at least one opening such that the spout extends from the at least one opening and radially outwardly from the at least one opening; providing a front impermeable layer; sealing the front impermeable layer to the rear impermeable layer around at least a substantial portion of the outer contacting edges to form the ostomy bag such that the spout extends predominantly into the interior of the ostomy bag formed.

In embodiments, the spout is fixedly attached to the bag via attachment to a plate positioned on an exterior of the bag.

In a third aspect the invention relates to a method for manufacturing an ostomy bag of the first aspect of the invention, comprising the steps of: providing an attachment plate having at least one opening; fixedly attaching a spout to a section of the edge of the at least one opening such that the spout extends away from the at least one opening and radially outwardly from the at least one opening; providing a bag having at least one aperture; and affixing the bag on the attachment plate to form an ostomy bag such that the spout extends predominantly into the interior of the ostomy bag through the aperture in the bag.

In embodiments, the bag is affixed to the attachment plate by at least one of permanent fixing and semi-permanent fixing. Suitably, permanent fixing is at least one of plastic welding, melting, screws, rivets, pins: and semi-permanent fixing is at least one of adhesive, clips, hooks, hook and loop tape, screw thread, bayonet fitting.

In a fourth aspect the invention relates to a method for attaching an ostomy bag to a patient with a stoma, comprising (1) affixing an ostomy seal to a patient such that it at least partially surrounds a stoma; (2) placing the ostomy bag of the first aspect of the invention on the ostomy seal such that at least one opening aligns with the patients' stoma. The steps of the method of this aspect of the invention may be performed in any suitable order.

In a fifth aspect the invention relates to a method for attaching an ostomy bag to a patient with a stoma, comprising (1) affixing an ostomy seal to the ostomy bag of the first aspect of the invention such that it at least partially surrounds the at least one opening; (2) placing the ostomy bag of step (1) on the patient such that the at least one opening aligns with the patients' stoma. The steps of the method of this aspect of the invention may be performed in any suitable order.

In a sixth aspect the invention relates to an attachment plate for use in an ostomy bag of the first aspect of the invention, comprising: a plate having at least one opening; and a spout positioned at least partially around the edge of the at least one opening; wherein the spout extends away from the at least one opening and radially outwardly from the at least one opening.

In embodiments the spout extends through the at least one opening such that an end of the spout rests against or near to a patient's skin when in use. In further embodiments, the spout is configured to direct ostomy output away from a patient's skin. In embodiments, the spout is angled to optimise collection of ostomy output and delivery of ostomy output into the ostomy bag.

In embodiments, the spout extends a perpendicular distance from the at least one opening by between 1 cm and 5 cm. In other embodiments, the spout is fixedly attached to the attachment plate.

In a seventh aspect the invention relates to an a method for attaching an ostomy bag to a patient with a stoma, comprising (1) affixing an ostomy seal to a patient such that it at least partially surrounds a stoma; (2) placing the attachment plate of the sixth aspect of the invention on the ostomy seal such that the at least one opening aligns with the patients' stoma; (3) placing an ostomy bag on the attachment plate. The steps of the method of this aspect of the invention may be performed in any suitable order.

In embodiments of the fourth, fifth and seventh aspect of the invention, the opening is adjusted to closely conform to the stoma of a patient.

In a eighth aspect, the invention relates to an ostomy attachment kit comprising an ostomy bag of the first aspect of the invention and an ostomy seal that is configured to at least partially surround a patient's stoma.

In a ninth aspect, the invention relates to an ostomy attachment kit comprising an attachment plate of the sixth aspect of the invention, an ostomy bag and an ostomy seal that is configured to at least partially surround a patient's stoma.

BRIEF DESCRIPTION OF THE DRAWINGS

One or more embodiments of the invention will now be described, by way of example only, with reference to the accompanying drawings, in which.

DETAILED DESCRIPTION OF THE INVENTION

Figure 1:
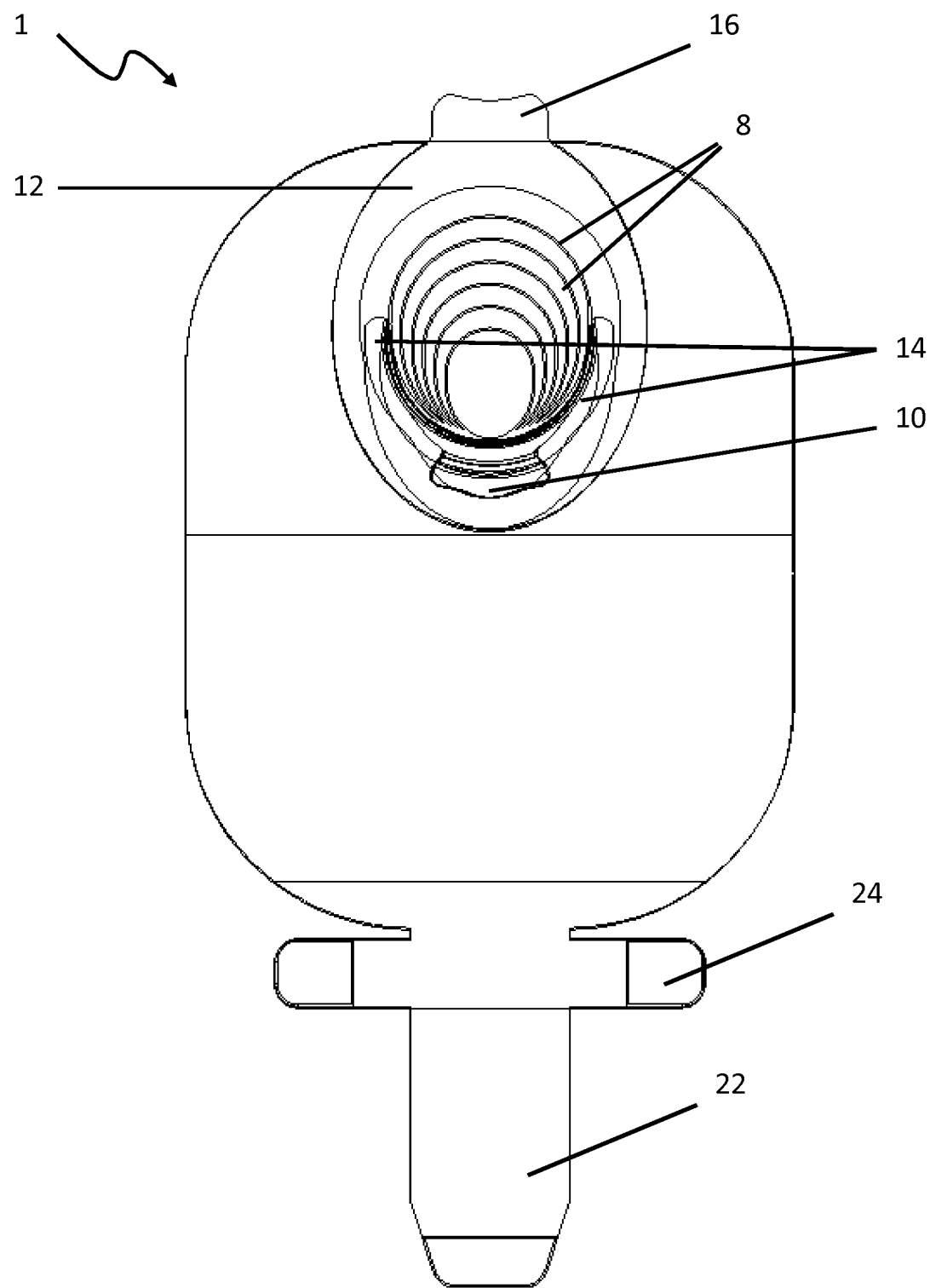
FIG. 1 of the drawings shows an ostomy bag 1 according to one embodiment of the invention.

Prior to setting forth the invention, a number of definitions are provided that will assist in the understanding of the invention. All references cited herein are incorporated by reference in their entirety. Unless otherwise defined, all technical and scientific terms used herein have the same meaning as commonly understood by one of ordinary skill in the art to which this invention belongs.

Unless otherwise indicated by context, the use herein of the singular is to be read to include the plural and vice versa. As such the terms "a", "an", "one or more", and "at least one" are used interchangeably herein.

As used herein, the term 'comprising' means any of the recited elements are necessarily included and other elements may optionally be included as well. 'Consisting essentially of' means any recited elements are necessarily included, elements which would materially affect the basic and novel characteristics of the listed elements are excluded, and other elements may optionally be included. 'Consisting of' means that all elements other than those listed are excluded. Embodiments defined by each of these terms are within the scope of this invention.

As used herein the term "absorbent" refers to a property of a material in which it can absorb water or other liquids. The term "absorbent material" refers to a material that has absorbent properties. The absorbent material may be materially affected by absorbing the water or other liquids, for example, the material may expand, distort, become unstable, degenerate or decompose. Examples of absorbent materials in the context of the present application are hydrocolloids and hydrogels. In contrast, the term "non-absorbent" refers to a property of a material in that it does not absorb water or other liquids. The term "non-absorbent material" refers to a material that has non-absorbent properties. The non-absorbent material may remain visibly and structurally unchanged after contact with these liquids. Examples of non-absorbent materials in the context of the present application are rubber, rubber-like materials, polyurethanes, silicones and thermoplastic elastomers. Further examples of non-absorbent materials may be thermosetting plastics and metals, such as shape-memory metals or foils.

As used herein the term "hydrocolloid" refers to a material that typically contain polymers such as polyisobutylene, and hydroactive particles such as sodium carboxymethyl cellulose, gelatine and pectin. The hydrocolloid swells on contact with hydrophilic fluids to form a semi-solid gel.

As used herein the term "resiliently deformable" refers to the ability of a material or a structure to bend or flex under a suitable force and when that force is removed to return substantially or exactly to the original shape or position.

As used herein the term "flexible" refers to the ability of a material or a structure to bend or flex under a suitable force.

As used herein the term "ostomy seal" or "seal" refers to a component that forms part of an ostomy attachment and acts to provide a fluid-tight seal between the stoma and the ostomy bag in which stomal output collects. Typically, an ostomy seal is biocompatible and is safe to use in contact with skin. Suitably, the ostomy seal has adhesive properties meaning it may adhere to the skin and/or other parts of the ostomy attachment. Suitably the ostomy seal is formed of an absorbent material such as hydrocolloid or a hydrogel. In embodiments, the ostomy seal is a planar annular ring (complete or broken one or more times by radial cuts) having an inner face and an outer face, wherein the outer face is generally perpendicular to the inner face, An inner wall or inner rim, generally perpendicular to the inner and outer face borders and/or surrounds a central opening in the ostomy seal. Concentrically arranged outside of, and generally parallel to the inner rim, is an outer wall or outer rim. Typically, the distance between the inner and the outer face is less than the distance between the diametrically opposed points on the outer rim.

As used herein the term "bag" refers to any form of receptacle suitable for collecting ostomy output. The term may be used interchangeably with the terms "pouch" and "receptacle". The bag is typically formed of a front liquid impermeable layer and a back liquid impermeable layer that are joined at their respective outer peripheries. The join may be a seal, partial or complete, around the circumference of the outer peripheries of the front and back liquid impermeable layers. One liquid impermeable layer, typically the back liquid impermeable layer, has an opening or aperture for entrance of the ostomy fluid and/or the stoma. The bag may have one or more additional openings, typically at the bottom when in use, that when required can be opened to empty the bag.

As used herein the term "in" in the context of a bag refers to the interior volume of the bag. The term "inward" or "inwardly" as used herein refers to a direction towards or into the interior volume of the bag. Conversely, As used herein the term "out" in the context of a bag refers to the space outside of the interior volume of the bag. The term "outward" or "outwardly" as used herein refers to a direction towards or out of the interior volume of the bag. The term "radially outward" or "radially outwardly" refers to a direction on a away from a defined object or centre thereof (or an approximation thereto).

As used herein, the term "front" refers to the side furthest from and/or facing away from the skin of the user as it would be in use. The term "rear" or "back" refers to the side closest to and/or facing the skin of the user as it would be in use. The term "bottom" or "inferior" refers to the lower end, or the lower end, optionally nearer the user's feet when in normal use. The term "top" refers to the upper end, or the higher end, optionally nearer the user's head when in normal use.

The present invention provides an improved ostomy bag that comprises a spout that projects into the interior volume of the bag and is able to direct the output from the stoma, typically under gravity, away from the skin to be collected into the ostomy bag. The ostomy bag of the present invention also provides for an ostomy bag that reduces or prevents stomal fluid splashing back onto an ostomy seal or skin, thereby providing an ostomy bag arrangement that has improved longevity in use and causes less skin irritation.

The ostomy bag of the present invention also acts to prevent blocking of the stoma by the front side of the bag reducing the propensity for leaks and so-called "pancaking" or "pattycaking". The present invention also provides for an improved ostomy bag that is easier for the patient to use and position.

Figure 2:
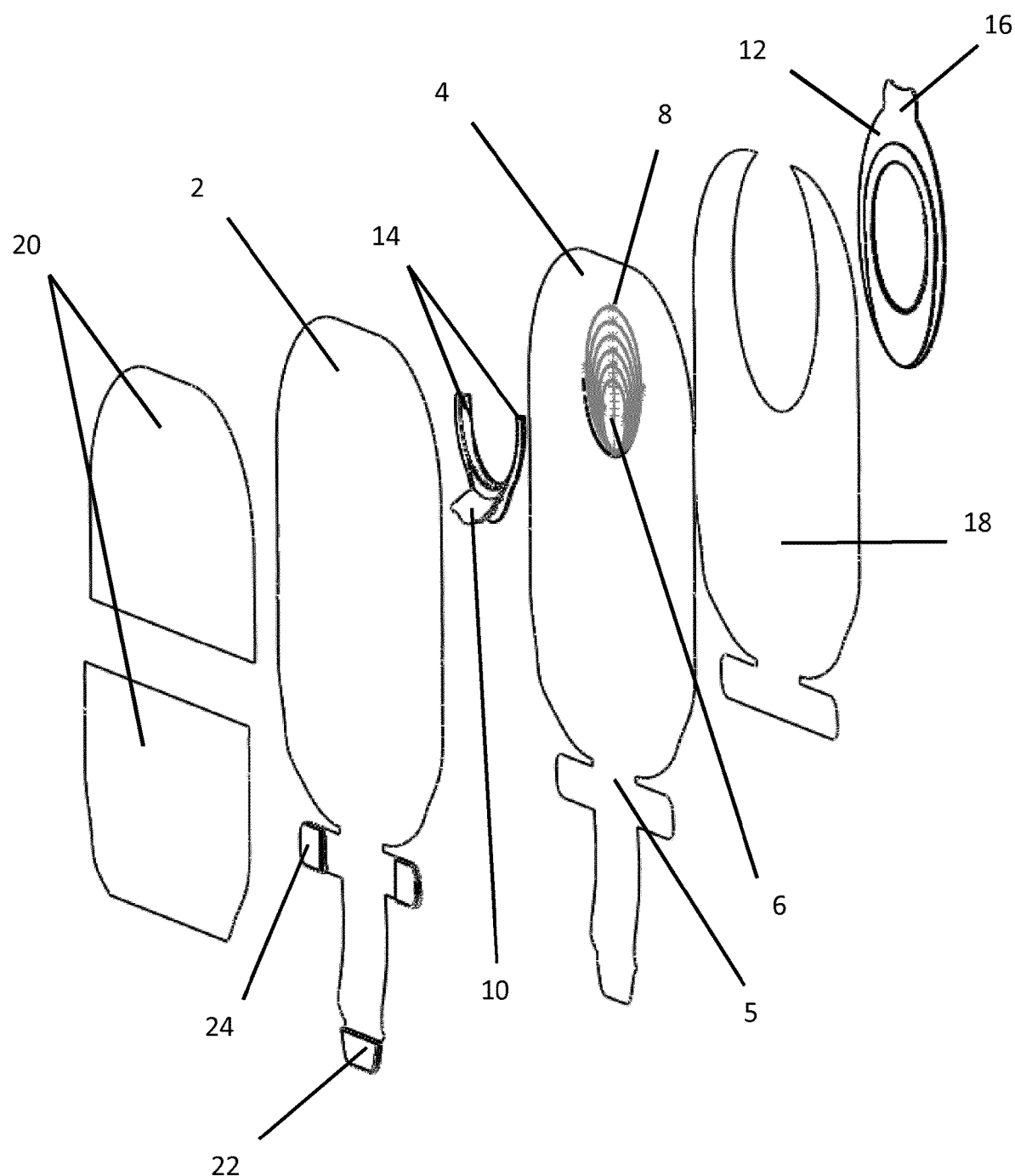
FIG. 2, shows the ostomy bag 1 of FIG. 1 with a cover on each side shown in exploded view.

FIG. 1 of the drawings shows an ostomy bag 1 according to one embodiment of the invention. FIG. 2, shows the ostomy bag 1 of FIG. 1 with a cover on each side shown in exploded view.

In embodiments, the ostomy bag 1 comprises a front liquid impermeable layer 2 and a rear liquid impermeable layer 4. The front and rear liquid impermeable layers 2, 4 are configured to be joined or sealed at substantially all of an outer contacting edge such that they form a bag or pouch. It is contemplated that the bag is substantially hollow. Nevertheless, it is also contemplated that the bag may have other contents, or the front and rear liquid impermeable layers may also be joined away from an outer contacting edge, provided the function of the bag to receive and contain the stomal output is not affected. In some embodiments, the front and rear liquid impermeable layers 2, 4 may be sealed around the entire outer contacting edge. Suitably, the impermeable layers 2, 4 are joined around the entire or whole outer contacting circumference except for an area 5 at the bottom of the bag or pouch to provide a means of emptying the contents of the bag when needed.

In embodiments, and in the embodiment shown in FIGS. 1 and 2, the rear impermeable layer 4 comprises an aperture or opening 6 for accepting ostomy output. Suitably, the opening 6 is in the top half of the rear impermeable layer 4. More suitably, the opening 6 is in the top 25% by length of the rear impermeable layer 4. The opening 6 may be in the top 20%, 15%, 10% or 5% by length of the rear impermeable layer 4.

In embodiments, the opening 6 is configured to embrace and surround the patient's stoma. The opening 6 may be adjusted in size by the user to that required so that it closely surrounds the stoma thereby providing an optimised fit. The generally circular markings 8 shown around the opening 6 in the embodiment shown in FIGS. 1 and 2 provide the user with a guide for adjusting the size of the opening 6. The size of the opening 6 may be adjusted by any suitable means. Suitably, the size is adjusted by cutting with scissors or as knife prior to use. Alternatively, the markings 8 can be perforated during manufacture so that each marked segment can be removed by manual tearing without tools. Each of the circular markings 8 share a bottom edge that is in line with the bottom edge of the opening 6 meaning that after adjustment, where necessary, the position of the bottom edge of the opening 6 remains unchanged. An optimised fit around the stoma by the opening 6 is one way in which the leakage of stomal fluid is minimised or prevented by the bag of the present invention.

In embodiments, and in the embodiment shown in FIGS. 1 and 2, arranged around the bottom edge of opening 6 is a spout 10. The spout 10 has an angled section that projects inwardly and radially outwardly from the centre (or approximation thereto) of the opening 6 into the ostomy bag 1. The angled section of the spout 10 projects at one end from, or close to, the bottom of the opening 6 at or close to skin level when in use. In this way, the spout 10 acts to direct the output from the stoma, under gravity, away from the skin into the ostomy bag 1.

The angled section of the spout 10 may be any suitable shape and size. Suitably, the angled section of the spout 10 is generally quadrangular in shape. In embodiments, the angled section of the spout 10 is between 1 cm and 5 cm long. Suitably, the angled section of the spout 10 is between 1 cm and 3 cm long. In embodiments, the angled section of the spout 10 has a maximum length of 0.5 cm or less, 1 cm, 1.5 cm, 2 cm, 2.5 cm. 3 cm, 3.5 cm, 4.0 cm or more. In embodiments, the angled section of the spout 10 has a maximum length of 7.0 cm or more, 6.5 cm, 6.0 cm, 5.5 cm, 5.0 cm or less. In further embodiments, the angled section of the spout 10 is between 1 cm and 5 cm wide. Suitably, the angled section of the spout 10 is between 1 cm and 3 cm wide. the angled section of the spout 10 has a minimum width of 0.5 cm or less, 1 cm, 1.5 cm, 2 cm, 2.5 cm. 3 cm, 3.5 cm, 4.0 cm or more. In embodiments, the angled section of the spout 10 has a maximum width of 7.0 cm or more, 6.5 cm, 6.0 cm, 5.5 cm, 5.0 cm or less.

Due to the angle of the spout 10 in certain embodiments, the height of the spout 10 (defined as the perpendicular distance between the opening 6 (or extended plane thereof) and the end of the spout furthest from the opening 6, is between 1 cm and 5 cm. Suitably, the height of the spout 10 is between 1 cm and 3 cm long. In embodiments, the minimum height of the spout 10 is 0.5 cm or less, 1 cm, 1.5 cm, 2 cm, 2.5 cm. 3 cm, 3.5 cm, 4.0 cm or more. In embodiments, the maximum height of the spout 10 is 7.0 cm or more, 6.5 cm, 6.0 cm, 5.5 cm, 5.0 cm or less.

The projection of the spout 10 into the ostomy bag 1 also acts to prevent the ostomy bag 1 from flattening and therefore in use promotes free passage of the ostomy output into the bag. "Pancaking" (or "pattycaking") occurs when stomal output sits on or around the stoma pad and fails to fall into the ostomy bag. This residual output can block or prevent further output which then can leak from the ostomy attachment and/or seal. Pancaking can be caused by the front layer of the bag resting over the stoma and therefore any means of preventing this occurring would be of benefit.

The spout 10 may be fixedly attached to the ostomy bag 1 in any suitable way. In embodiments, and as shown in FIGS. 1 and 2, the spout 10 is fixedly attached to an attachment plate or plate 12 on the exterior of the ostomy bag 1. In an embodiment, a portion of the rear liquid impermeable layer 4 comprising opening 6 is sandwiched between the spout 10 and the attachment plate 12 thereby fixing both the spout 8 and the attachment plate 12 to the ostomy bag 1. In alternative embodiments the attachment plate 12 and the spout 10 maybe formed as a single unitary piece and the attached to an ostomy bag by any suitable means, for example, plastic moulding, adhesive, semi-permanent attachment such as hook and loop tape, or mechanical attachments such as pins, screws of fixings.

In embodiments, the spout 10 comprises one or more curved arms 14 that project from a central portion of the spout 10. The curved arms 14 act to direct stomal output to the angled section of the spout and increase the surface area of the spout 10 that may attach to the attachment plate 12 and thereby strengthen the fixing to the attachment plate 12. The fixing between the spout 10 and the attachment plate 12 may be by any suitable means, for example, chemical such as plastic or heat welding or adhesive; or mechanical such as via clips, or screws.

In some embodiments, the spout 10 may extend outwardly from the ostomy bag 1 to the end, or just beyond, the face of the attachment plate 12 near the skin to optimise collection of ostomy output and prevent or reduce the amount of ostomy output contacting the skin.

The spout 10 and attachment plate 12 may be formed of any suitable material. They may be formed of the same or a different material, provided the choice of material does not prevent suitable attachment therebetween. Suitably, the spout 10 and the attachment plate 12 are each formed of a non-absorbent material that is resistant to deformation and/or degradation from contact with output from the stoma. Suitably, the spout 10 and the attachment plate 12 are formed of a resiliently deformable or flexible material. Any material with the required properties would be suitable to form the spout 10 and the attachment plate 12; specific examples include rubber, rubber-like materials, polyurethanes, silicones and thermoplastic elastomers.

In embodiments, the front and rear liquid impermeable layers 2, 4 are formed of a transparent, flexible plastic sheet.

Materials for use in ostomy bags are well known and any material suitable for use in an ostomy bag is to be considered suitable for the invention.

The attachment plate 12 provides a surface away from the ostomy bag suitable for securing to an ostomy bag seal. The ostomy bag seal is commonly a complete annular ring, or can be split into two or more pieces. The ostomy bag seal is typically flexible to assist in adapting the inner circumference of the ostomy bag seal to obtain an optimised fit around the stoma.

In an embodiment, an inner surface or face of an ostomy bag seal abuts and adheres to the skin and the outer face, substantially parallel to and opposite the inner face, provides an attachment site for the attachment plate 12, either directly or via a further seal already affixed to the attachment plate 12. The inner and outer circumference of the or each seal may be selected such that sufficient surface area is provided on the annular seal 4 to result in good adherence of the outer face of the ostomy bag seal with the attachment plate 12.

In embodiments, an ostomy bag seal (not shown) may be provided on the attachment plate 12, or the attachment plate 12 may provide a surface for attachment to an ostomy seal already affixed to the skin or provided separately. In a further embodiment, an ostomy seal may be placed on the patient, and a further ostomy seal may be placed on the attachments plate to surround the opening 6 and the two seals are brought into contact in substantially aligned registry at which point they fuse together to form the seal. When the ostomy bag 1 is provided with a seal on the attachment plate 12, the seal is suitably hydrocolloid to fuse with the same material commonly used in ostomy seals.

The attachment plate 12 may have suitable fixings (not shown) for attachment of a securing belt or other means of physical attachment to the patient, that holds the bag in place on the patient when in use, either in combination with or instead of the adhesive seal described above. In embodiments, the attachment plate has a finger grip 16 for holding the ostomy bag 1, and to assist the use in removal of the ostomy bag 1 when replaced. The finger grip 16 may be positioned slightly inwardly of the face of the attachment plate to allow the user to grip both sides.

The ostomy bag 1 may be covered with a coating to strengthen the front and rear liquid impermeable layers 2, 4 and/or to shield or obscure the contents of the ostomy bag 1 from view when in use. The cover may also provide strengthening to reduce the risk of puncturing of the ostomy bag 1, or may be for decoration or to improve the aesthetic look or the feel of the ostomy bag 1. Any form of covering is contemplated. In FIGS. 1 and 2, the embodiment shown has a cover material 18 that is fixed to the rear impermeable layer 4, and a cover material 20 that is fixed to the front impermeable layer 2. In the embodiment shown the cover material 20 is formed and fixed in two over-lapping parts such that a window is left through which the contents can be viewed if desired. The coating 18, 20 may be formed of any suitable material. Suitable materials are non-woven fabrics such as cotton, nylon, polyester, or mixtures thereof. In alternative embodiments, the ostomy bag may be covered with a removable cover.

In embodiments, for example the embodiment shown in FIGS. 1 and 2, the area 5 at the bottom of the ostomy bag to allow emptying of the contents is sealed in use by a tongue 22 and retaining arms 24 arrangement. The tongue 22 is rolled up or folded from the end until positioned between the arms 24. The arms 24 are then fixed to each other at the ends but any suitable means, for example, hook and loop tape or adhesive, thereby retaining the rolled tongue 22 in a sealed position. When the bag is to be emptied, the arms 24 are released and the tongue 22 unrolled to allow the contents of the ostomy bag to be drained.

The ostomy bag of the present invention may optionally comprise a filter system (not shown) which allows the release of gases from the interior of the ostomy bag to prevent "ballooning". The filter may comprise means for absorbing odours (for example charcoal), or preventing escape of liquids.

The present invention provides an improved ostomy bag that comprises a spout that is able to direct the output from the stoma, typically under gravity, away from the skin to be collected into the ostomy bag. By more effectively protecting the absorbent, suitably hydrocolloid, seal material the non-absorbent spout section reduces the risk of the hydrocolloid breaking down and thereby improves the longevity of the ostomy seal saving costs for the patient and/or the healthcare provider. The present invention also provides for an improved ostomy attachment that is easier for the patient to use and position.

In a further advantage, the spout provides a physical barrier that prevents or reduces the stomal output splashing back on the annular seal and/or skin.

It is a further advantage of the present invention that the protruding nature of the spout separates the sides of the ostomy bag so that both parts of the bag cannot come into contact with each other in the area around the stoma. This reduces or mitigates the risk of the flow of the output into the bag from being impeded by the sides of the bag coming together. This can be a significant issue with prior art ostomy bags, the effect being known as "pancaking".

The fact that the advantages of: (1) collecting and directing stomal output away from the annular seal and/or skin; (2) avoiding splashback of stomal fluid from the bag onto the annular seal and/or skin; and (3) preventing pancaking all derive from a single feature of a central section, in particular, when the central section is in the form of a spout, is a particular advantage of the present invention.

It should be understood that the different embodiments of the invention described herein can be combined where appropriate and that features of the embodiments of the invention can be used interchangeably with other embodiments where appropriate.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the scope of the invention as defined by the claims.

The invention claimed is:

1. An ostomy bag for collecting output from a stoma, wherein the ostomy bag comprises:
   at least one opening for accepting ostomy output; and
   a spout positioned at least partially around the edge of the at least one opening;
   wherein the spout extends away from the at least one opening and radially outwardly from the at least one opening, into the interior of the ostomy bag; and
   wherein the spout is directly fixedly attached to an interior surface of the ostomy bag.

2. The ostomy bag of claim 1, wherein the spout extends outwardly from the interior of the ostomy bag such that an outer end of the spout rests against or near to a patient's skin when in use.

3. The ostomy bag of claim 1, wherein the spout is configured to direct ostomy output away from a patient's skin and into the ostomy bag.

4. The ostomy bag of claim 1, wherein the spout is angled to optimise collection of ostomy output and delivery of ostomy output into the ostomy bag.

5. The ostomy bag of claim 1, wherein the spout extends a perpendicular distance from the at least one opening into the ostomy bag by between 1 cm and 5 cm.

6. The ostomy bag of claim 1, wherein the spout comprises at least one flexible arm that extends around the at least one opening.

7. The ostomy bag of claim 6, wherein the spout comprises two flexible arms that extend around the at least one opening.

8. The ostomy bag of claim 1, wherein the ostomy bag has generally circular concentric markings around the at least one opening to provide the user with a guide for adjusting the size of the at least one opening.

9. The ostomy bag of claim 8, wherein the generally circular markings share an edge with the at least one opening adjacent with the spout.

10. An ostomy attachment kit comprising an ostomy bag of claim 1 and an ostomy seal that is configured to at least partially surround a patient's stoma.

* * * * *